(12) United States Patent
Cline-Rew

(10) Patent No.: US 10,610,328 B2
(45) Date of Patent: Apr. 7, 2020

(54) SLIDING RADIOLOGICAL MARKER DOCUMENTATION SYSTEM TO LEGALLY LABEL X-RAY IMAGES

(71) Applicant: Charlotte Cline-Rew, Austin, TX (US)

(72) Inventor: Charlotte Cline-Rew, Austin, TX (US)

( * ) Notice: Subject to any disclaimer, the term of this patent is extended or adjusted under 35 U.S.C. 154(b) by 19 days.

(21) Appl. No.: 16/034,579

(22) Filed: Jul. 13, 2018

(65) Prior Publication Data

US 2020/0015929 A1    Jan. 16, 2020

(51) Int. Cl.
*A61B 90/00* (2016.01)
*G03B 42/04* (2006.01)

(52) U.S. Cl.
CPC ...... *A61B 90/39* (2016.02); *A61B 2090/3966* (2016.02); *G03B 42/047* (2013.01)

(58) Field of Classification Search
CPC .................. G03B 42/047; A61B 90/39; A61B 2090/3966
See application file for complete search history.

(56) References Cited

U.S. PATENT DOCUMENTS

| 2,858,446 A | * | 10/1958 | Parish | .................. | G03B 42/047 |
| | | | | | 378/165 |
| 2016/0374642 A1 | * | 12/2016 | Yamashita | ............... | A61B 6/08 |
| | | | | | 378/204 |

* cited by examiner

*Primary Examiner* — Chih-Cheng Kao
(74) *Attorney, Agent, or Firm* — Dunlap Bennett & Ludwig PLLC

(57) ABSTRACT

An imaging marker positioning system is provided. The imaging marker positioning system embodies a plurality of markers slidable along an elastic band. Guide clips may removably secure the elastic band to the imaging device so that a first portion of the elastic band may be disposed within a field of view of the imaging device. A user may slide one or more predetermined markers onto the first portion, whereby an image of the marker is captured in the resulting X-ray image. Additionally, the user may adjust the guide clips and/or the elastic band to reposition the first portion relative to the field of view of the imaging device.

6 Claims, 4 Drawing Sheets

SLIDING RADIOLOGICAL MARKER DOCUMENTATION SYSTEM TO LEGALLY LABEL X-RAY IMAGES

BACKGROUND OF THE INVENTION

The present invention relates to X-ray devices and, more particularly, to a non-adhesive sliding radiological marker documentation system to legally label x-ray images with appropriate "Left" or "Right" side of the body markers.

When using imaging techniques, such as X-ray, it is common practice to capture images of markers along with the captured X-ray image so as to identify and document the subject matter documenting the Left or Right side of the body within captured X-ray image. Current methods use medical tape to place markers on imaging devices for such purposes, which is unsightly, messy and lacks versatility. Replacing worn out tape every few days, and losing markers is a constant problem for technologist. Moreover, sticky residue makes the equipment look dirty. In other words, the old-fashioned taping system results in lost markers, sticky residue, and a bad impression on patients, who may start questioning the technical sophistication of the medical facility. Furthermore, the current method of labeling the X-ray image with left or right markers is frustrating when the tape loses sufficient adherence, causing the marker to not stay in place, possibly requiring that the X-ray image be repeated. In the context of fluoroscopic procedures, which requires moving the marker multiple times during the exam, the propensity of current imaging marker solutions to fail, requiring multiple marker moves results in increasing the radiation exposure to the patient and the technologist and Radiologist.

As can be seen, there is a need for a non-adhesive sliding radiological marker documentation system to legally label X-ray images. The sliding marker system uses no tape to position the marker, and so no sticky residue builds up on the x-ray equipment or lost personal markers; rather, the present invention embodies markers adapted to slide up and down or from side to side for selective marker placement, which saves time and allows for tighter collimation during live fluoroscopic imaging and other imaging procedures.

Instead of sticky tape, the sliding marker system embodies a strip of elastic onto which the markers slide, making it easy to slide the marker into position each time the anatomy requires a change, while keeping the markers handy at all times. This system is clean and leaves no sticky residue. Markers are kept in one place ready to use with a simple slide up, down or left or right.

SUMMARY OF THE INVENTION

In one aspect of the present invention, an imaging marker positioning system including an elastic band; one or more image markers easily slidable when engaged with the elastic band; each image marker providing a marker indicium, the marker indicium being made from a radiopaque material; the elastic band being radiolucent and the elastic band being removable secured to an imaging device so that a first portion of the elastic band is movable through a field of view of said imaging device.

In another aspect of the present invention, a method of marking a captured image from an imaging device using the above-mentioned imaging marker positioning system; releasably attaching a plurality of guide clips so as to movably secure the elastic band to the imaging device so that the first portion movable; and selectively sliding the one or more image marker along the first portion.

These and other features, aspects and advantages of the present invention will become better understood with reference to the following drawings, description and claims.

DETAILED DESCRIPTION OF THE INVENTION

Figure 1:
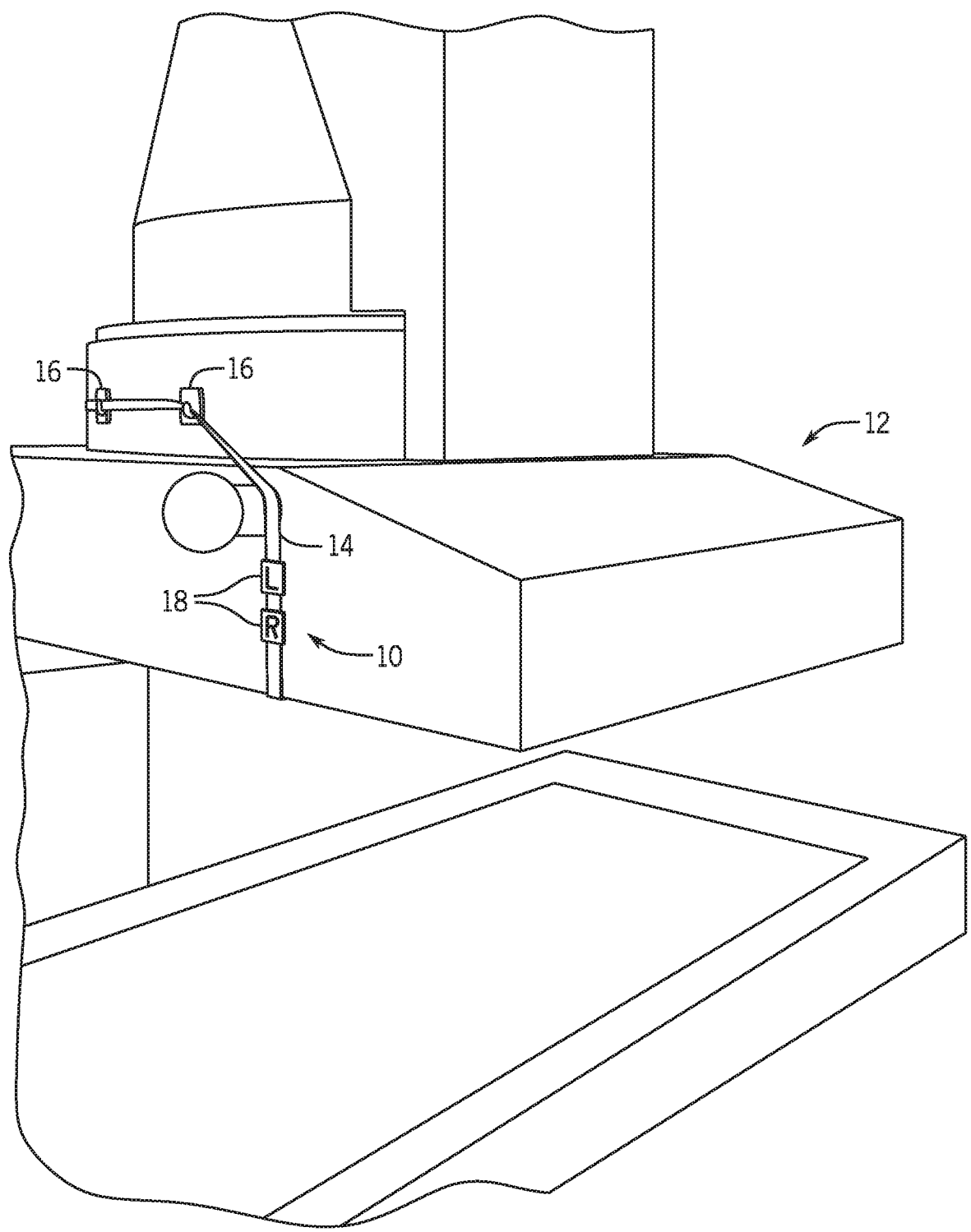
FIG. 1 is a perspective view of an exemplary embodiment of the present invention, shown in use.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, an embodiment of the present invention provides an imaging marker positioning system embodying a plurality of markers slidable along an elastic radiolucent band. Guide clips may removably secure the elastic band to the imaging device so that a first portion of the elastic band may be disposed within a field of view of the imaging device. A user may either slide one or more predetermined markers onto the first portion, whereby an image of the marker is captured in the resulting imaging image. Additionally, the user may adjust the guide clips and/or the elastic band to reposition the first portion relative to the field of view of the imaging device.

Referring to FIGS. 1 through 5, the present invention may include an imaging marker positioning system 10 providing a plurality of markers 18 operatively engaged along an elastic band 14 to slide and be selectively positioned along the elastic band 14. Each marker 18 provides a clip 22 movable between a sliding condition and a positioning condition, facilitating the operative engagement of the marker 18 and the elastic band 14. A first portion 30 of the elastic band 14 is moveable into a field of view of an imaging device so that any marker 18 disposed along the first portion 30 will be captured in the resulting image of the imaging device 12. The imaging device 12 may be an X-ray device, such as a fluoroscopic device or the like, used in the field of radiology. The resulting images being X-ray images and other images used in the medical field.

Figure 2:
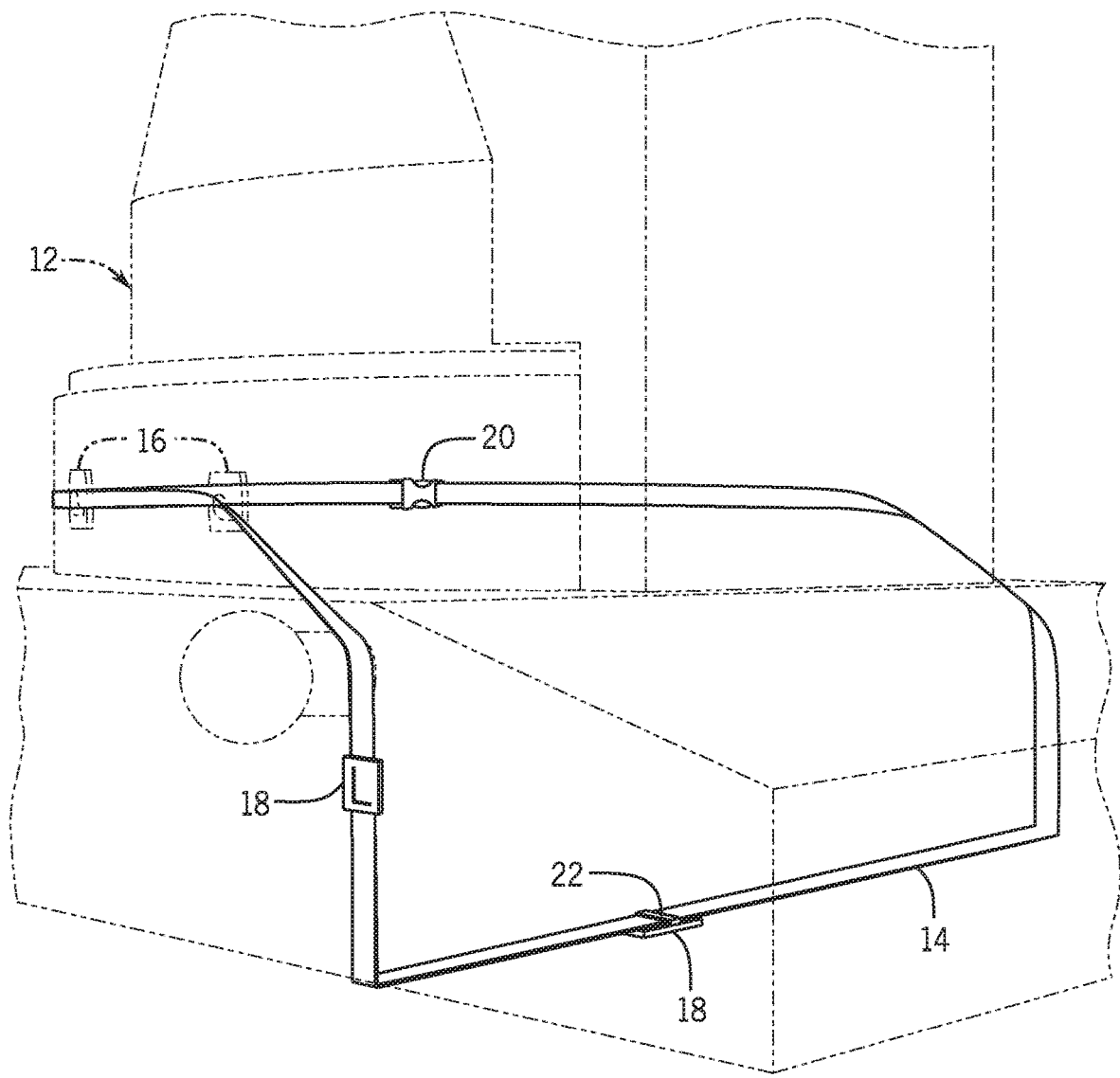
FIG. 2 is a perspective view of an exemplary embodiment of the present invention, shown in use with an imaging device shown in phantom, illustrating that the elastic band 14 may extend for up to ten or more feet.
Figure 4:
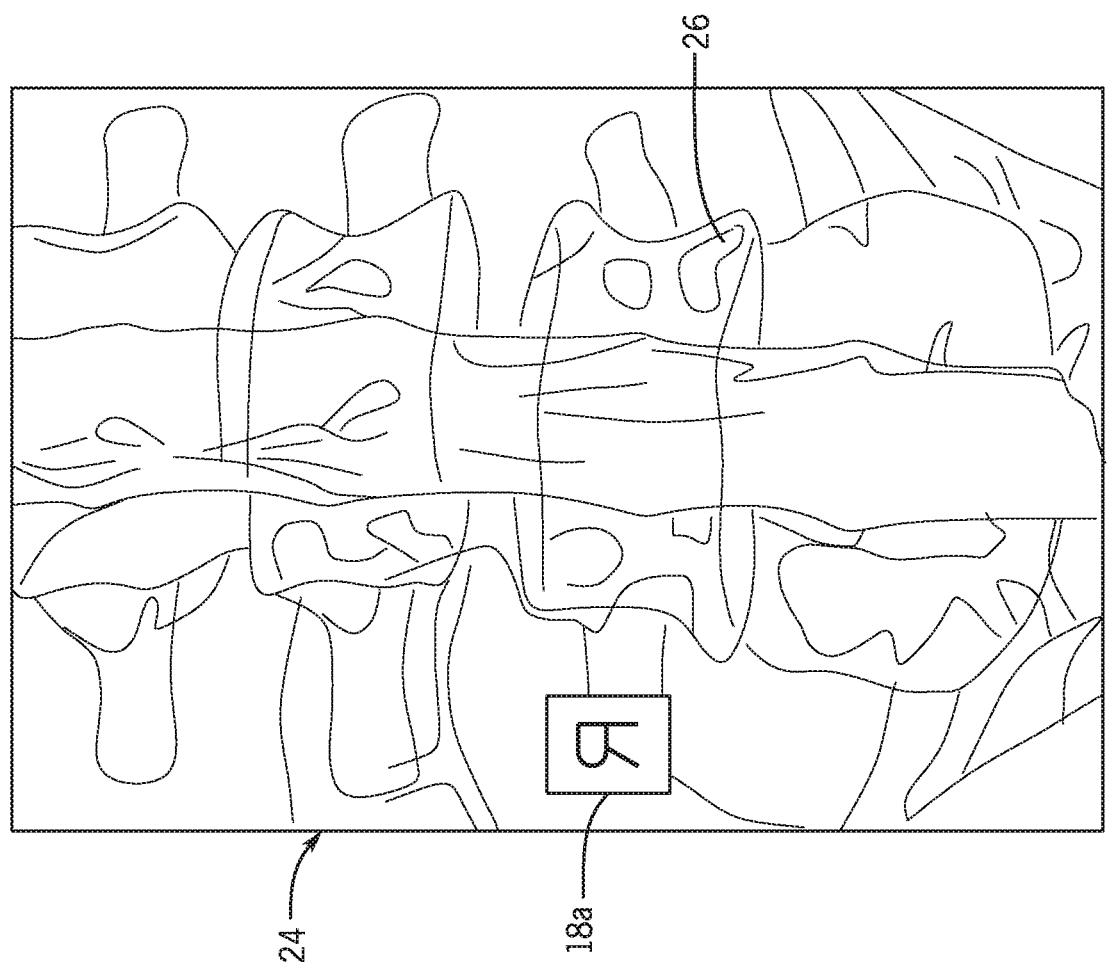
FIG. 4 is a view of an exemplary embodiment of a photographic plate of the present invention.
Figure 3:
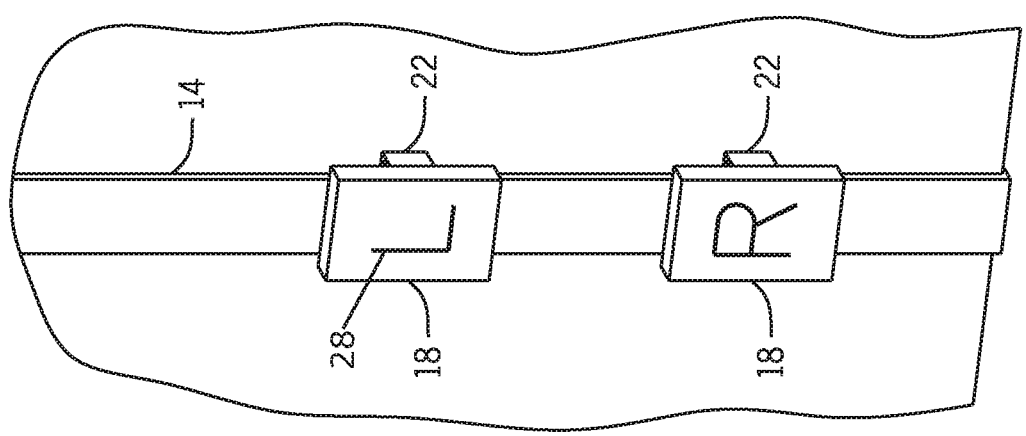
FIG. 3 is a detail perspective view of an exemplary embodiment of the present invention.
Figure 5:
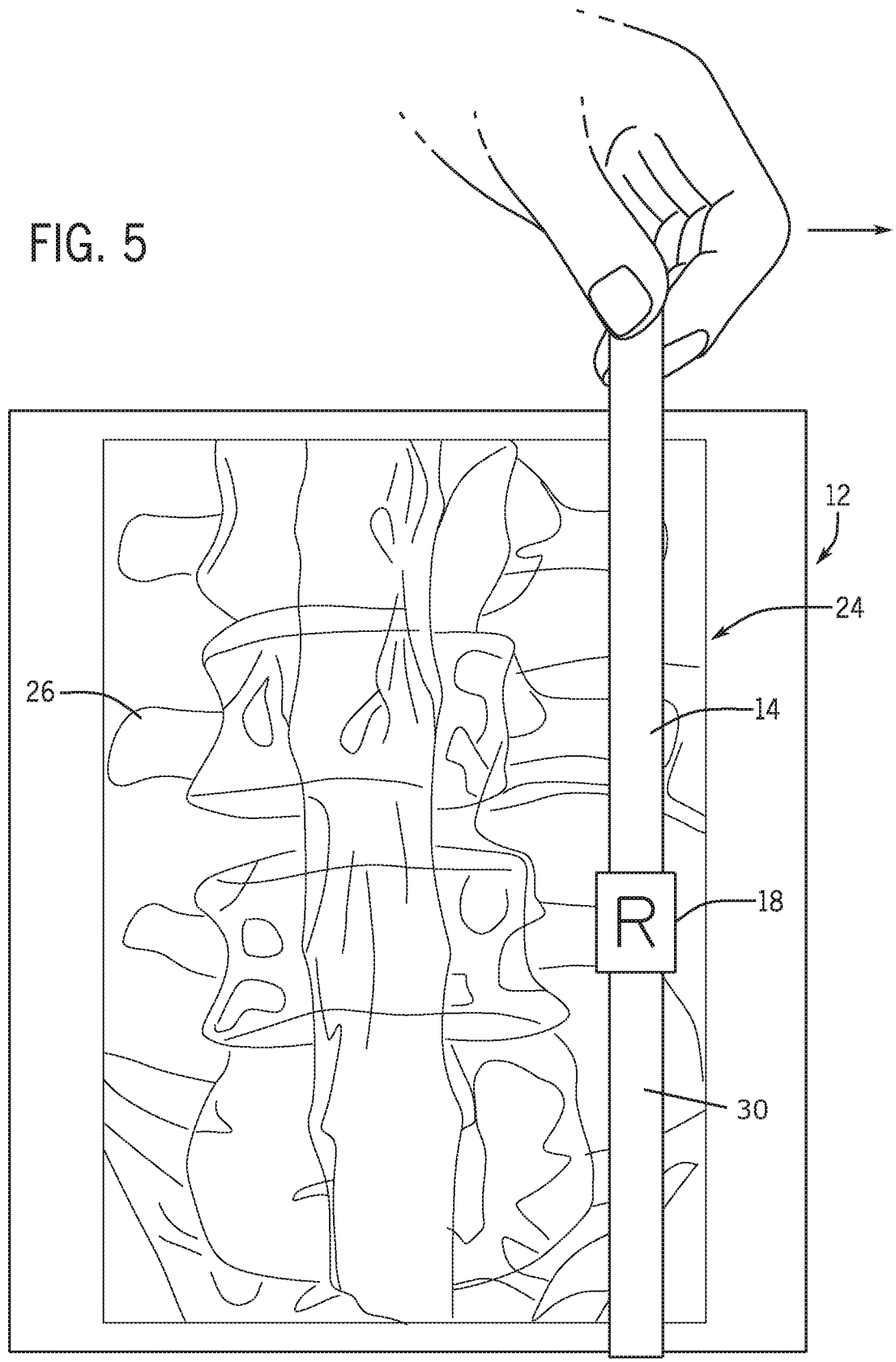
FIG. 5 is a view of an exemplary embodiment of the photographic plate of the present invention, demonstrating how a marker can be moved to or from outside the exposure area.

The elastic band 14 may be made of radiolucent material so that a X-ray image thereof is invisible or mostly invisible, transparent or translucent. The elastic band 14 may extend to opposing releasable fasteners 20, forming a loop when the releasable fasteners 20 are engaged. When disengaged from the releasable fasteners 20 the elastic band 14 may be strapped about an imaging device 12 with the aid of guide clips 16, as illustrated in FIGS. 1 and 2. Each The guide clip 16 may have a removable connector to removably engage the imaging device 12. The guide clips 16 may provide hooks for holding a relevant portion of the elastic band 14 at a certain elevation. The guide clips 16 may be repositioned along the imaging device 12 to accommodate for various components of the x-ray device 12, such as a fluoroscopic tower, as well as to reposition a first portion 30 of the elastic band 14 so that it extends through the view of the image capturing device so that a marker image 18a of each lead marker 18 positioned on the first portion 30 is captured on the resulting x-ray image 26. As a corollary, the remaining second portion of the elastic band 14 would be outside the view of the image capturing device, and thus is where markers 18 that the technologist does not need in the current resulting x-ray image 26 are disposed during the image capture process. These markers are essentially parked or stored out of the field of view, for later use.

Each marker 18 may provide marking indicia 28, such a 'R' indicating 'Right' or a 'L' indicating 'Left' to facilitate the imaging marking process. The marking indicia is made of X-ray opaque material or "radiopaque" material, such as lead, so as to produce an image on the film negative.

A method of using the invention may include the following. The imaging marker positioning system 10 disclosed above may be provided. A user may secure the sliding marker system 10 around the image capturing device 12.

Repositioning the guide clip(s) 16 to move the first portion 30 with the desired marker(s) 18 within the view of the image capturing device 12 enables placing the marker image 18a of a desired marker 18 into the resulting x-ray image 26. Such repositioning of the elastic band 14 facilitates making larger movements of the elastic band 14. Selectively tweaking the placement of the first portion 30 and the second portion relative to the view of the image capturing device 12 may be achieved by gently repositioning the guide clips 16.

The user may position of the elastic band 14 so that the first portion 30 extends across the field of view of the image capturing device, whereby the lead markers 18 are orientated parallel or 'flat' relative to (or against) this view. In certain embodiments, the first portion 30 may be positioned adjacent the photographic file (e.g., X-ray plate/detector) when capturing the image. The marker indicia 28 are selected by the medical professional or technologist. The user then selectively slides the desired markers 18 onto the first portion 30 and into view of the image capturing device 12 as needed. In certain embodiments, the user may slide the 'Right' marker 18 upside down when performing prone images. That way, when flipping the resulting x-ray images 26, it will be correctly displayed. The user may place the desired markers 18 on the band 14, slide the ones not being used out of view, onto the second portion, for later use.

The imaging marker positioning system 10 enables quick fine tuning of the marker placement. When performing myelograms or lumbar punctures, tight collimation is essential. By having the system 10 embodied in the present invention, the user can slide the 'Right' or 'Left' marker tightly up against the spine or body part being examined. When imaging moves from the lumbar area to the cervical area, or prone to laterals, the user can adjust the marker placement with a slight slide of the elastic band 14. The imaging marker positioning system 10 may also be used to engage a radiographic wall stands (a/k/a "wall Bucky")

Properly securing the imaging marker positioning system 10 to the x-ray device 12 includes measuring the diameter of that device's components: such as the fluoroscopic tower or wall Bucky, and then cutting the elastic strip 14 to length accordingly. The user would attach the male and female ends of the releasable fastener 20 onto each end of the elastic band 14. Then the user may wrap the elastic band 14 about the imaging device 12 and pull through until taught around the related equipment. Then the user would utilize the guide clips 16 for selectively engaging portions of the elastic band 14 to further facilitate properly oriented the first portion 30 of the elastic band relative to the view of the image capturing device.

The user would selectively slide a desired marker 18 into position along the first portion 30. In certain embodiments, the positioning of the markers 18 along the first portion 30 includes from head to foot, or just off center from left to right. When the imaging device 12 is activated, for example the fluoroscopic tower is in motion, the user could move the marker 18 from outside of the direct beam to place the marker as close to the body part as possible. The fluoroscopist could then collimate the X-ray beam to the anatomy which reduces scatter radiation. This reduction in scatter radiation directly improves image quality and reduces radiation exposure to the patient and to the imaging staff. The user would strive to continue to refine the marker placement throughout the exam. If the patient is moved to the supine position, the user could slide the marker 18 to the other side of the imaging device 12.

The imaging marker positioning system 10 can produce excellent marker placement on images which can gain respect from the referring physicians. This is a great opportunity to market the imaging company as professional and one that takes pride in their work.

It should be understood, of course, that the foregoing relates to exemplary embodiments of the invention and that modifications may be made without departing from the spirit and scope of the invention as set forth in the following claims.

What is claimed is:

1. An imaging marker positioning system, comprising:
    an elastic band;
    one or more imaging markers slidably engaged with the elastic band;
    each imaging marker providing a marker indicium, the marker indicium being made from an X-ray opaque material;
    the elastic band being radiolucent; and
    the elastic band being removable secured to an imaging device so that a first portion of the elastic band is movable through a field of view of said imaging device.

2. The imaging marker positioning system of claim 1, further comprising a cooperating removable fastener attached to each of the two opposing ends of the elastic band.

3. The imaging marker positioning system of claim 1, wherein the X-ray opaque material is lead.

4. A method of marking a captured image from an imaging device, comprising the steps of:
    providing the imaging marker positioning system of claim 1;
    releasably attaching a plurality of guide clips so as to movably secure the elastic band to the imaging device so that the first portion movable; and
    selectively sliding the one or more imaging markers along the first portion.

5. The method of claim 4, further comprising the step of adjusting at least one of the guide clips so as to selectively move the first portion within the field of view.

6. The method of claim 4, further comprising the step of sliding the one or more imaging markers from the first portion so as to be outside the field of view.

\* \* \* \* \*